United States Patent
Hershenfield et al.

(10) Patent No.: US 10,533,222 B2
(45) Date of Patent: Jan. 14, 2020

(54) METHODS AND COMPOSITIONS FOR DETECTION OF TARGETS FOR AUTOIMMUNE DISEASE

(71) Applicant: University Health Network, Toronto (CA)

(72) Inventors: Brian Hershenfield, Thornhill (CA); Tak W. Mak, Toronto (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 0 days.

(21) Appl. No.: 14/641,358

(22) Filed: Mar. 7, 2015

(65) Prior Publication Data

US 2015/0315642 A1    Nov. 5, 2015

Related U.S. Application Data

(60) Provisional application No. 61/949,927, filed on Mar. 7, 2014.

(51) Int. Cl.
| | |
|---|---|
| C12N 15/113 | (2010.01) |
| A61K 38/17 | (2006.01) |
| A61K 39/00 | (2006.01) |
| C12Q 1/68 | (2018.01) |
| C12Q 1/6883 | (2018.01) |
| A61K 49/00 | (2006.01) |
| C12Q 1/6886 | (2018.01) |
| G01N 33/50 | (2006.01) |

(52) U.S. Cl.
CPC .......... *C12Q 1/6883* (2013.01); *A61K 38/177* (2013.01); *A61K 49/0008* (2013.01); *C12N 15/1138* (2013.01); *C12Q 1/6886* (2013.01); *G01N 33/5088* (2013.01); *A61K 2039/507* (2013.01); *C12N 2310/14* (2013.01); *C12N 2320/30* (2013.01); *C12Q 2600/106* (2013.01); *C12Q 2600/158* (2013.01); *G01N 2333/82* (2013.01)

(58) Field of Classification Search
None
See application file for complete search history.

(56) References Cited

U.S. PATENT DOCUMENTS

2011/0306655 A1* 12/2011 Janssen ............... A61K 31/713
514/44 A
2014/0294792 A1* 10/2014 Prabhakar ............ C12N 5/0637
424/93.71

FOREIGN PATENT DOCUMENTS

WO    WO/2013/149167    * 3/2013

OTHER PUBLICATIONS

McDyer, et al. (1999) J. Immunology, v.162(6):3711-7.*
Siegert I., et al., Electroporation of siRNA into Mouse Bone Marrow-Derived Macrophages and Dendritic Cells. In: Li S., Cutrera J., Heller R., Teissie J. (eds) Electroporation Protocols. Methods in Molecular Biology. (Year: 2014 ).*
Condamine, T. et al., "Tmem176B and Tmem176A are associated with the immature state of dendritic cells," *Journal of Leukocyte Biology*, Sep. 2010, vol. 88, pp. 507-515.
Hopp, A-K. et al., "Self-antigen presentation by dendritic cells in autoimmunity," *Frontiers in Immunology*, Feb. 13, 2014, vol. 5, Article 55, pp. 1-14.
Inaba, K. et al., "Generation of Large Numbers of Dendritic Cells from Mouse Bone Marrow Cultures Supplemented with Granulocyte/Macrophage Colony-stimulating Factor," *J. Exp. Med.*, Dec. 1992, vol. 176, pp. 1693-1702.
International Search Report for International Patent Application No. PCT/IB2015/000912, dated Oct. 9, 2015, 4 pages.
Jantsch, J. et al., "Small interfering RNA (siRNA) delivery into murine bone marrow-derived dendritic cells by electroporation," *J Immunol Methods*, 2008, vol. 337, pp. 71-77.
Ke, B. et al., "β-Catenin Regulates Innate and Adaptive Immunity in Mouse Liver Ischemia-Reperfusion Injury," *Hepatology*, 2013, vol. 57, pp. 1203-1214.
Lonza, "Amaxa® Mouse Dendritic Cell Nucleofector® Kit," 2009, 4 pages.
Lutz, M.B. et al, "An advanced culture method for generating large quantities of highly pure dendritic cells from mouse bone marrow," *J Immunol Methods*, 1999, vol. 223, pp. 77-92.
Mashreghi, M-F. et al., "Inhibition of Dendritic Cell Maturation and Function is Independent of Heme Oxygenase 1 but Requires the Activation of STAT3," *The Journal of Immunology*, 2008, vol. 180, pp. 7919-7930.
Moita, C.F. et al., "RNAi screen for kinases and phosphatases that play a role in antigen presentation by dendritic cells," *European Journal of Immunology*, 2012, vol. 42, pp. 1843-1849.
Paul, P. et al., "A Genome-wide Multidimensional RNAi Screen Reveals Pathways Controlling MHC Class II Antigen Presentation," *Cell*, 2011, vol. 145, pp. 268-283.
Singhal, J. et al., "Suppression of Dendritic Cell-mediated Response by Genes in Calcium and Cysteine Protease Pathways during *Mycobacterium tuberculosis*, Infection," *The Journal of Biological Chemistry*, Mar. 30, 2012, vol. 287, No. 14, pp. 11108-11121.
Zheng, X. et al., "Treatment of Autoimmune Arthritis Using RNA Interference-Modulated Dendritic Cells," *The Journal of Immunology*, 2010, vol. 184, pp. 6457-6464.

* cited by examiner

*Primary Examiner* — Jennifer Pitrak McDonald

(57) ABSTRACT

The present invention is directed to methods and compositions for identifying targets for induction of self-tolerance and treatment of autoimmune disease.

7 Claims, 17 Drawing Sheets

METHODS AND COMPOSITIONS FOR DETECTION OF TARGETS FOR AUTOIMMUNE DISEASE

CROSS-REFERENCE TO RELATED APPLICATIONS

This application claims the benefit of U.S. Ser. No. 61/949,927, filed Mar. 7, 2014, the content of which is incorporated herein by reference in its entirety.

BACKGROUND OF THE INVENTION

Autoimmune diseases are a major cause of morbidity and mortality, afflicting approximately 3-10% of the population in Western countries. There are more than 80 distinct autoimmune diseases, most of which are chronic conditions that often manifest debilitating and life-threatening complications. Current therapies for autoimmune diseases are suboptimal because they often cause generalized immunosuppression, which predisposes the recipient to serious infections and cancer. Moreover, these therapies fail to correct the fundamental biological defect underlying autoimmune disease pathogenesis: loss of immunologic self-tolerance. The outcome of autoantigen recognition by the immune system (self-tolerance or autoimmune disease) is largely determined by the activation state of the dendritic cells (DCs) that uptake, process, and present autoantigens to autoreactive T cells. In particular, activation of dendritic cells to an immunogenic phenotype is necessary for the full activation of naïve autoreactive T cells, and thus necessary for the initiation of autoimmune disease. There is a need for better understanding of the cellular and molecular triggers and mechanisms of DC activation, which could catalyze the development of novel therapies to induce self-tolerance in patients with autoimmune disease.

SUMMARY OF THE INVENTION

Accordingly, the present invention provides a method for identifying one or more target genes that modulate activation state of dendritic cells, the method comprising: (a) transfecting immature bone marrow-derived dendritic cells (BMDCs) with an siRNA library; and (b) detecting activation of the BMDCs, thereby identifying one or more target genes that modulate activation state of dendritic cells. In one embodiment, the detecting step (b) is conducted on BMDCs that have not received any additional stimulation other than the transfecting step (a).

In a further embodiment and in accordance with the above, the detecting step (b) includes detection of a dendritic cell intrinsic effector function. In a still further embodiment, the dendritic cell intrinsic effector function comprises expression of one or more of a member selected from the group consisting of: IL-12/23-p40, CCD80, CD86, and MHCII.5.

In a still further embodiment and in accordance with any of the above, the detecting activation step (b) is conducted using flow cytometry.

In a yet further embodiment and in accordance with any of the above, the immature BMDCs transfected in step (a) are cultured to minimize baseline activation.

In a further embodiment and in accordance with any of the above, the methods of the invention include, subsequent to the in vitro screening phase, a further in vivo validating phase involving validating the one or more target genes that modulate activation state of dendritic cells in an in vivo screen to determine whether the one or more target genes are a candidate target for treatment of autoimmune disease. In an exemplary embodiment, the in vivo screen includes the steps of (i) providing BMDCs that lack the candidate gene; (ii) exposing the BMDCs lacking the candidate gene to activating stimulus; (iii) transferring the BMDCs from step (iii) to an animal model; (iv) assessing whether the animal model develops an autoimmune disease, thereby validating the target gene as a candidate target for treatment of autoimmune disease. In a further embodiment, the animal model is a model for a member selected from the group consisting of autoimmune diabetes, multiple sclerosis, and rheumatoid arthritis.

In a yet further embodiment and in accordance with any of the above, the siRNA library used in the in vitro phase of the screen comprises siRNAs directed to transmembrane receptors.

DETAILED DESCRIPTION OF THE INVENTION

Figure 1:
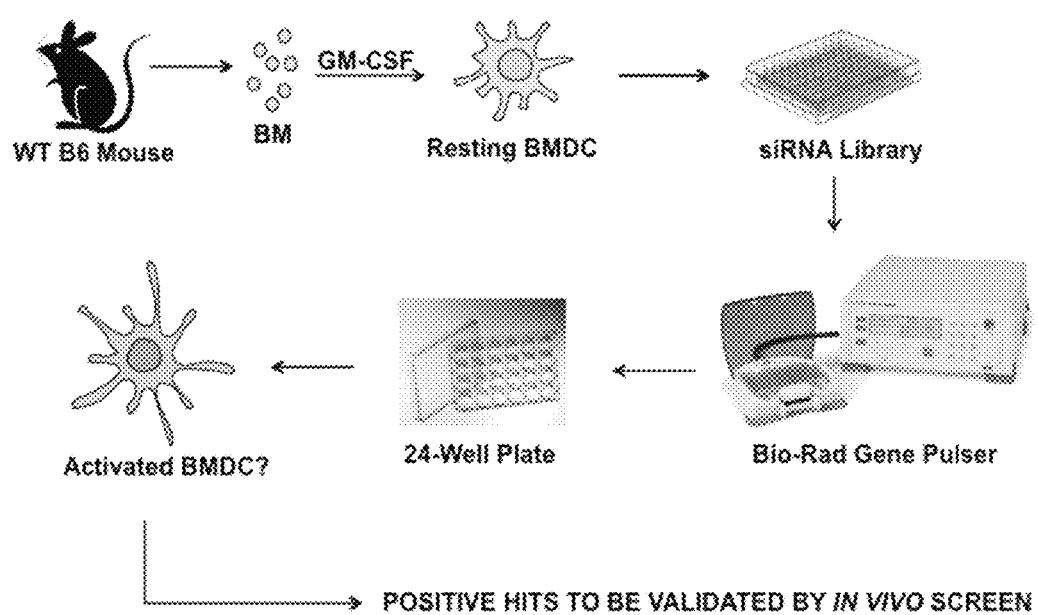
FIG. 1 is an exemplary illustration of an embodiment of the invention.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, phage display, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), *Lehninger, Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

A "composition" may include any substance comprising an agent or compound and is also intended to encompass any combination of an agent or compound and other substances, including a carrier, e.g., compound or composition, inert (for example, a detectable agent or label) or active, such as an adjuvant, diluent, binder, stabilizer, buffers, salts, lipophilic solvents, preservative, adjuvant or the like. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, asparagine, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

"BMDC" as used herein refers to Bone marrow-derived dendritic cell.

The term pharmaceutically acceptable carrier (or medium), which may be used interchangeably with the term biologically compatible carrier or medium, refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio. Pharmaceutically acceptable carriers suitable for use in the present invention include liquids, semi-solid (e.g., gels) and solid materials (e.g., cell scaffolds and matrices, tubes sheets and other such materials as known in the art and described in greater detail herein). These semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways.

As used herein, the term "patient" or "subject" intends an animal, a mammal or yet further a human patient. For the purpose of illustration only, a mammal includes but is not limited to a human, a simian, a murine, a bovine, an equine, a porcine or an ovine.

As used herein, the term "oligonucleotide" or "polynucleotide" refers to a short polymer composed of deoxyribonucleotides, ribonucleotides or any combination thereof. Oligonucleotides are generally at least about 10, 15, 20, 25, 30, 40, 50, 60, 70, 80, 90, 100 or more nucleotides in length. An oligonucleotide may be used as a primer or as a probe.

As used herein, the term "sample" or "test sample" refers to any liquid or solid material containing nucleic acids. In suitable embodiments, a test sample is obtained from a biological source (i.e., a "biological sample"), such as cells in culture or a tissue sample from an animal, most preferably, a human.

"Substantially homogeneous" describes a population of cells in which more than about 50%, or alternatively more than about 60%, or alternatively more than 70%, or alternatively more than 75%, or alternatively more than 80%, or alternatively more than 85%, or alternatively more than 90%, or alternatively, more than 95%, of the cells are of the same or similar phenotype. Phenotype can be determined by a pre-selected cell surface marker or other marker.

Although the present invention is described primarily with reference to specific embodiments, it is also envisioned that other embodiments will become apparent to those skilled in the art upon reading the present disclosure, and it is intended that such embodiments be contained within the present inventive methods.

In one aspect, the present invention provides methods for screening for proteins that encode proteins that are key to maintaining dendritic cells (DCs) in an inactivated state. Without being limited by mechanism, the screens of the present invention are based in part on the fact that the outcome of T cell antigen recognition, i.e., immunity versus tolerance and the phenotype of the resulting immune response, depends on the activation state of DCs. Only DCs that have been activated by Pattern associated molecular pattern proteins (PAMPs) or Danger-associated molecular pattern proteins (DAMPs) via their Pattern recognition receptors (PRRs)—thereby upregulating costimulatory molecules and producing cytokines—can initiate a primary immune response by activating naïve T cells. Thus, there is no autoimmune disease without T cell activation, and there is no T cell activation without DC activation. As such, the methods and compositions of the present invention screen for target genes that, when silenced, result in DC activation, thus identifying targets that are key for prevention and/or treatment of autoimmune disease.

In general, in the methods of the present invention, libraries of siRNAs are used to transfect dendritic cells. This screen is in preferred embodiments a high volume, high throughput screen in which different libraries are used to transfect thousands to millions of dendritic cells. After transfection, the cultures are screened for activated dendritic cells using methods such as a fluorescent detection (e.g., by utilizing a "knock-in" of a fluorescent protein for detection by automatic cell sorters and the like), and targets are identified that are key to maintaining dendritic cells in the inactivated state. Potential targets are then validated in an in vitro and/or an in vivo study. In vivo studies include screens to determine whether putative targets attenuate or exacerbate disease symptoms in mouse models. Models of particular use for in vivo validation studies in accordance with the invention include models of autoimmune diseases such as rheumatoid arthritis, EAE, and diabetes.

FIG. 1 provides an overview of a general embodiment of the in vitro phase of the siRNA library screen in BMDCs. A small interfering RNA (siRNA) library is electroporated into resting BMDCs. One gene is targeted in each BMDC sample. After 48 hours of putative gene silencing, BMDCs are assayed in vitro for evidence of maturation. As will be appreciated, FIG. 1 provides an overview of one exemplary embodiment of the in vitro phase of the screen, and as is described in further detail herein, different elements of the embodiment pictured in FIG. 1 can be altered and/or optimized and be encompassed by the presently disclosed invention. For example, instead of siRNA libraries, other types of libraries that dampen or eliminate expression can be used, including other kinds of RNA interference such as microRNA (miRNA) and short hairpin RNA (shRNA). In addition, instead of electroporation, other methods for incorporating these nucleic acid libraries into the BMDCs can be used, including without limitation lipofection.

Figure 2:
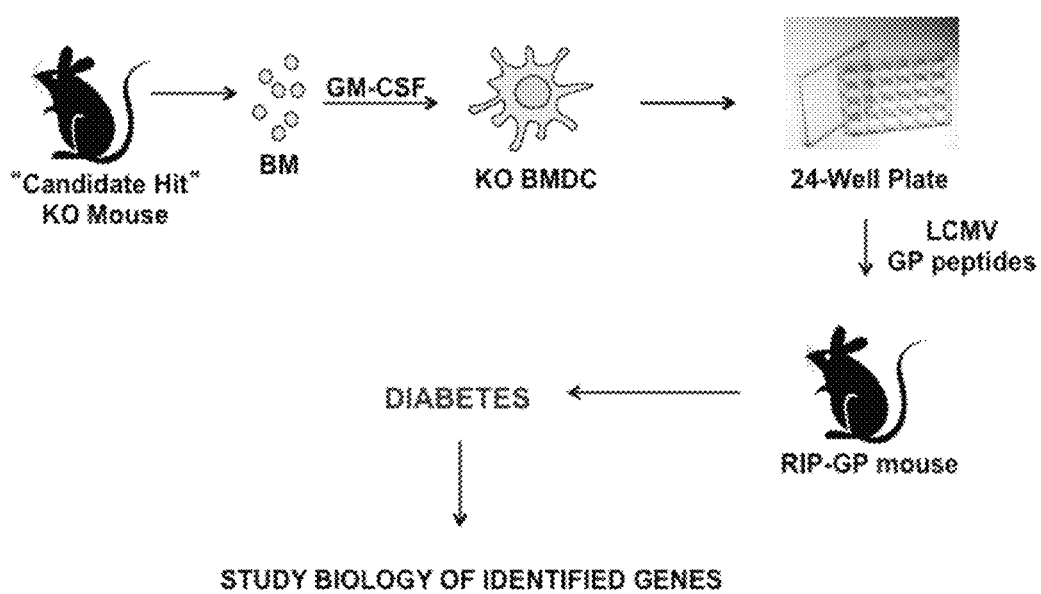
FIG. 2 is an exemplary illustration of an embodiment of the invention.

FIG. 2 provides an overview of a general embodiment of the in vivo phase of screening methods of the present invention. In this embodiment, BMDCs are generated in vitro from a mouse strain in which a candidate gene hit from the in vitro screen is genetically ablated. These knockout BMDCs are pulsed with Lymphocytic choriomeningitis virus (LCMV) glycoprotein (GP) peptides with or without Toll-like receptor (TLR) stimulation, then adoptively transferred into Rat insulin promoter-lymphocytic choriomeningitis virus glycoprotein (RIP-GP) mice and monitored for the development of autoimmune diabetes. In a different embodiment of the in vivo screen (not shown), WT BMDCs are generated in vitro, then the candidate gene hit is silenced by siRNA. The siRNA-transfected BMDCs are then pulsed with LCMV GP peptides with or without TLR stimulation, then adoptively transferred into RIP-GP mice and monitored for the development of autoimmune diabetes. The RIP-GP DC vaccination model of autoimmune diabetes is an example of an in vivo system in which autoreactive T cell fate and disease outcome are regulated by the activation state of the DC. Thus, it is a robust in vivo system for testing the activation state and immunogenicity of DCs.

The two phase screening approach outlined above provides an advantage by achieving a balance between (1) high-throughput, and (2) specificity, sensitivity, and cost-efficiency.

The invention disclosed herein readily lends itself to high efficiency, high-throughput siRNA library screening. The commercial availability of siRNA libraries, the use of a 96-well electroporator, and the implementation of adjustable multi-channel pipetting techniques all promote high efficiency workflow. The use of adjustable multi-channel pipettes is especially strategic because it enables the rapid transfer of samples between the 96-well electroporation plates and the pre-warmed, culture medium-containing 24-well plates. This rapid transfer also promotes cell viability by (1) minimizing the electroporated BMDCs' exposure time to potentially cell-damaging pH extremes near the electroporator electrodes, and (2) bathing the BMDCs in warm serum-containing medium as soon as possible after electroporation.

In general, methods of the invention include a step in which expression of one or more genes is attenuated or silenced. The phrase "attenuating expression" with reference to a gene or an mRNA as used herein means administering or expressing an amount of interfering RNA (e.g., an siRNA) to reduce translation of a target mRNA into protein, either through mRNA cleavage or through direct inhibition of translation. The terms "inhibit," "silencing," and "attenuating" as used herein refer to a measurable reduction in expression of a target mRNA or the corresponding protein as compared with the expression of the target mRNA or the corresponding protein in the absence of an interfering RNA of the invention. The reduction in expression of the target mRNA or the corresponding protein is commonly referred to as "knock-down" and is reported relative to levels present following administration or expression of a non-targeting control RNA (e.g., a non-targeting control siRNA). Knockdown of expression of an amount including and between 50% and 100% is contemplated by embodiments herein. However, it is not necessary that such knock-down levels be achieved for purposes of the present invention.

Knock-down is commonly assessed by measuring the mRNA levels using quantitative polymerase chain reaction (qPCR) amplification or by measuring protein levels by western blot or enzyme-linked immunosorbent assay (ELISA). Analyzing the protein level provides an assessment of both mRNA cleavage as well as translation inhibition. Further techniques for measuring knock-down include RNA solution hybridization, nuclease protection, northern hybridization, gene expression monitoring with a microarray, antibody binding, radioimmunoassay, and fluorescence activated cell analysis.

In one embodiment, a single interfering RNA is delivered to decrease target mRNA levels. In other embodiments, two or more interfering RNAs targeting the mRNA are administered to decrease target mRNA levels. In further embodiments, libraries containing over 1000, 2000, 3000, 4000, 5000, 6000, 7000, 8000, 9000, 10000 and more interfering RNAs are used in screening methods of the present invention.

As used herein, the terms "interfering RNA" and "interfering RNA molecule" refer to all RNA or RNA-like molecules that can interact with RISC and participate in RISC-mediated changes in gene expression. Examples of other interfering RNA molecules that can interact with RISC include short hairpin RNAs (shRNAs), single-stranded siRNAs, microRNAs (miRNAs), picoRNAs (piRNAs), and dicer-substrate 27-mer duplexes. Examples of "RNA-like" molecules that can interact with RISC include siRNA, single-stranded siRNA, miRNA, piRNA, and shRNA molecules that contain one or more chemically modified nucleotides, one or more non-nucleotides, one or more deoxyribonucleotides, and/or one or more non-phosphodiester linkages. Thus, siRNAs, single-stranded siRNAs, shRNAs, miRNAs, piRNA, and dicer-substrate 27-mer duplexes are subsets of "interfering RNAs" or "interfering RNA molecules."

The term "siRNA" as used herein refers to a double-stranded interfering RNA unless otherwise noted. Typically, an siRNA used in a method of the invention is a double-stranded nucleic acid molecule comprising two nucleotide strands, each strand having about 10 to about 28 nucleotides—in further embodiments, the siRNA is about 10, 11, 12, 13, 14, 15, 16, 17, 18, 19, 20, 21, 22, 23, 24, 25, 26, 27, or 28 nucleotides in length. Typically, an interfering RNA used in a method of the invention has a length of about 19 to 49 nucleotides. The phrase "length of 19 to 49 nucleotides" when referring to a double-stranded interfering RNA means that the antisense and sense strands independently have a length of about 19 to about 49 nucleotides, including interfering RNA molecules where the sense and antisense strands are connected by a linker molecule. In further embodiments, the length of the interfering RNA, including siRNA, is about 10-100, 20-90, 30-80, 40-70, 50-60 nucleotides in length.

The interfering RNA used in a delivery system and method of the invention can be unmodified or can be chemically stabilized to prevent degradation in the lysosome or other compartments in the endocytic pathway.

Single-stranded interfering RNA has been found to effect mRNA silencing. Therefore, embodiments of the present invention also provide for administration of a single-stranded interfering RNA. The single-stranded interfering RNA has similar lengths as for the double-stranded interfering RNA cited above. The single-stranded interfering RNA has a 5' phosphate or is phosphorylated in situ or in vivo at the 5' position. The term "5' phosphorylated" is used to describe, for example, polynucleotides or oligonucleotides having a phosphate group attached via ester linkage to the C5 hydroxyl of the sugar (e.g., ribose, deoxyribose, or an analog of same) at the 5' end of the polynucleotide or oligonucleotide.

Single-stranded interfering RNAs can be synthesized chemically or by in vitro transcription or expressed endogenously from vectors or expression cassettes as described herein in reference to double-stranded interfering RNAs. 5' Phosphate groups may be added via a kinase, or a 5' phosphate may be the result of nuclease cleavage of an RNA. A hairpin interfering RNA is a single molecule (e.g., a single oligonucleotide chain) that comprises both the sense and antisense strands of an interfering RNA in a stem-loop or hairpin structure (e.g., a shRNA). For example, shRNAs can be expressed from DNA vectors in which the DNA oligonucleotides encoding a sense interfering RNA strand are linked to the DNA oligonucleotides encoding the reverse complementary antisense interfering RNA strand by a short spacer. If needed for the chosen expression vector, 3' terminal T's and nucleotides forming restriction sites may be added. The resulting RNA transcript folds back onto itself to form a stem-loop structure.

Interfering RNAs may differ from naturally-occurring RNA by the addition, deletion, substitution or modification of one or more nucleotides. Non-nucleotide material may be bound to the interfering RNA, either at the 5' end, the 3' end, or internally. Such modifications are commonly designed to increase the nuclease resistance of the interfering RNAs, to improve cellular uptake, to enhance cellular targeting, to assist in tracing the interfering RNA, to further improve stability, to reduce off-target effects, or to reduce the potential for activation of the interferon pathway. For example, interfering RNAs may comprise a purine nucleotide at the ends of overhangs. Conjugation of cholesterol to the 3' end of the sense strand of an siRNA molecule by means of a pyrrolidine linker, for example, also provides stability to an siRNA.

Further modifications include a biotin molecule, a peptidomimetic, a fluorescent dye, or a dendrimer, for example.

Nucleotides may be modified on their base portion, on their sugar portion, or on the phosphate portion of the molecule and function in embodiments of the present invention. Modifications include substitutions with alkyl, alkoxy, amino, deaza, halo, hydroxyl, thiol groups, or a combination thereof, for example. Nucleotides may be substituted with analogs with greater stability such as replacing a ribonucleotide with a deoxyribonucleotide, or having sugar modifications such as 2' OH groups replaced by 2' amino groups, 2' O-methyl groups, 2' methoxyethyl groups, or a 2'-O, 4'-C methylene bridge, for example. Examples of a purine or pyrimidine analog of nucleotides include a xanthine, a hypoxanthine, an azapurine, a methylthioadenine, 7-deazaadenosine and O- and N-modified nucleotides. The phosphate group of the nucleotide may be modified by substituting one or more of the oxygens of the phosphate group with nitrogen or with sulfur (phosphorothioates). Modifications are useful, for example, to enhance function, to improve stability or permeability, to reduce off-target effects, or to direct localization or targeting.

In certain embodiments, an interfering molecule of the invention comprises at least one of the modifications as described above.

Interfering RNA target sequences (e.g., siRNA target sequences) within a target mRNA sequence can be selected using available design tools as discussed above. Interfering RNAs corresponding to a target sequence are then tested in vitro by transfection of cells expressing the target mRNA followed by assessment of knockdown as described herein. The interfering RNAs can be further evaluated in vivo using animal models as described herein.

In general, and in accordance with any of the description herein, the screening methods of the invention utilize BMDCs. In further embodiments, the cells used are immature BMDCs but are not bone marrow precursors—in other words, the cells used in the methods described herein are fully dendritic cells, albeit immature (inactivated) cells.

In certain embodiments, prior to transfection with the siRNA libraries, the BMDCs are maintained in culture conditions that minimize the baseline maturation level to allow for a high-dynamic range screen. In certain embodiments, Lactate dehydrogenase (LDH) levels in the BMDC cultures are maintained at about 200-800, 250-750, 300-700, 350-650, 400-600, 450-550 mU/mL. In further embodiments, Serum glutamic oxaloacetic transaminase (SGOT) concentrations were maintained at about 5-60, 10-55, 15-50, 20-45, 25-40 mU/mL. In still further embodiments, LDH levels are about 200, 300, 400, 500, 600, 700, 800, 900 mU/mL. In yet further embodiments, SGOT levels are maintained in the BMDC cultures at about 10, 20, 30, 40, 50, 60 mU/mL. Generally, the LDH and SGOT levels are controlled through choice of fetal bovine serum (FBS) used in the cultures, although any methods known in the art can be used to control these concentration levels. As will be appreciated, any combination of LDH and SGOT concentrations as described herein can be used in order to minimize baseline maturation levels of BMDCs in accordance with present invention.

In further embodiments, GM-CSF was removed from the BMDC culture medium on day 10, at the time when the BMDCs are transferred to tissue culture-treated plates for a further period of culture. This can serve to eliminate potential stimulatory effects of GM-CSF and thereby further minimize baseline BMDC maturation level.

In general, siRNA libraries are incorporated into BMDCs through transfection by electroporation. As will be appreciated, other methods of transfection known in the art may also be used.

In embodiments using electroporation, different exponential pulse waveforms may be used to optimize transfection efficiency. In some embodiments, an exponential pulse waveform of about 400 V/200 μF is used. As will be appreciated, this waveform can be empirically altered to customize transfection efficiency.

Transfection efficiency and effectiveness can also be affected by the time point at which electroporation is administered during the lifetime of a BMDC culture. In certain embodiments, electroporation of the siRNA libraries is conducted at day 7-8 of the culture. In further embodiments, the electroporation is administered at about day 5-15, 6-14, 7-13, 8-12, 9-11 of the culture. In yet further embodiments, the electroporation is administered at about day 5, 6, 7, 8, 9, 10, 11, 12, 13, 14, 15, 16, 17, 18, 19, 20 of the culture.

In further embodiments, the concentration of siRNA used during transfection is altered to maximize transfection efficiency. In still further embodiments, about 4000-10000, 5000-9000, 6000-7000 nM of siRNA is used. In yet further embodiments, at least 2000, 2500, 3000, 3500, 4000, 4500, 5000, 5500, 6000, 7000, 8000, 9000, 10000 nM of siRNA is used. In still further embodiments, about 3000, 3200, 3400, 3600, 3800, 4000, 4100, 4300, 4500, 4700, 4900, 5000, 5300, 5600, 5900, 6200, 6500, 7000 nM of siRNA is used.

In certain aspects, the screening methods of the present invention identify siRNA that effectively silence genes responsible for maintaining BMDCs in an inactivated state. Thus, the present screening methods utilize markers of BMDC activation. BMDC activation in methods of the present invention is determined using robust in vitro readouts. In some embodiments, such readouts include assays for classic costimulatory molecules, including without limitation CD80 and CD86. Such molecules are effective indicators of BMDC activation, because full activation of naive T cells requires the interaction of CD80 and CD86 on the BMDC surface with CD28 on the T cell surface. In addition, CD80 and CD86 are reliably and significantly upregulated on BMDCs that have been stimulated via TLRs, the prototypic PRRs. An additional advantage of using CD80 and CD86 as assays for BMDC activation is that detection of such molecules can be accomplished using methods amenable to high throughput large scale activity, including flow cytometric detection of cell-surface molecules stained with fluorochrome-conjugated antibodies to analyze BMDC surface expression of CD80 and CD86. Additional markers for BMDC activation of use in methods of the present invention include Major histocompatibility complex class II (MHCII), dextran (DX) uptake, and IL-12/23-p40 production. As will be appreciated, any other known markers of BMDC activation can also be used in the methods of the present invention.

In further embodiments, the readouts of BMDC activation are conducted in the absence of any further stimulation other than the initial transfection of the siRNA libraries. In other words, the readout of BMDC activation identifies only activation initiated by the silencing of one or more genes by transfection of the siRNA libraries, and not by any additional stimulation from other methods known in the art, including stimulation with TLR ligands, *M. tuberculosis* antigens, or *M. tuberculosis* infection.

Figure 16:
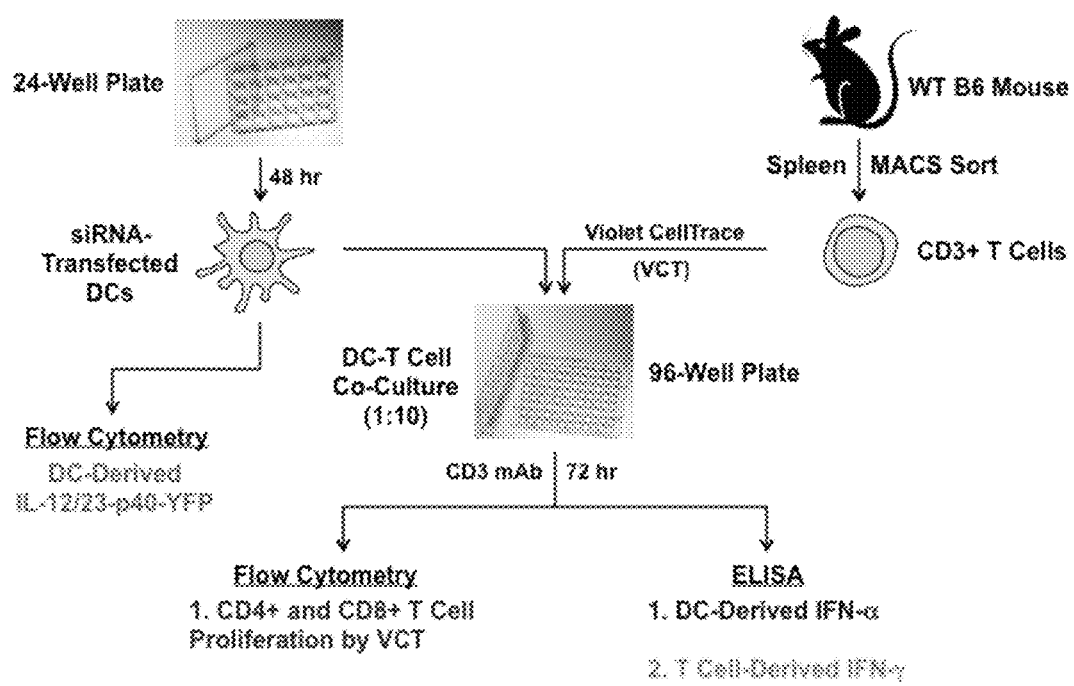
FIG. 16 is a schematic illustration of an embodiment of the invention.

In some embodiments, further validation studies of screens utilizing the above-described markers of BMDC activation. Such further validations include without limitation ELISA-based analyses, and T cell proliferation assays as a functional correlate to BMDC-derived IL-12/23-p40 production (see FIG. 16). In such assays, purified CD3+ T cell cells were co-cultured with siRNA-transfected BMDCs in the presence of low-dose CD3 monoclonal antibody stimulation, and T cell proliferation was measured by flow cytometric analysis of Violet CellTrace dye dilution. As schematically illustrated in FIG. 16, BMDCs generated in vitro from an IL-12/23-p40-YFP knock-in mouse are transfected with an siRNA library. After 48 hours of putative gene silencing, one portion of the siRNA-transfected BMDCs are analyzed for IL-12/23-p40-YFP expression by flow cytometry. In parallel, splenic CD3+ T cells are purified and stained with Violet CellTrace, then co-cultured with a second portion of the siRNA-transfected BMDCs in the presence of low-dose CD3 monoclonal antibody stimulation. After 72 hours of co-culture, T cell proliferation is analyzed by flow cytometry. Co-culture supernatants are harvested for future cytokine ELISA analysis.

In a still further embodiment and in accordance with any of the above, the methods of the invention include, subsequent to the in vitro screening phase, a further in vivo validating phase involving validating the one or more target genes that modulate activation state of dendritic cells in an in vivo screen to determine whether the one or more target genes are a candidate target for treatment of autoimmune disease. In an exemplary embodiment, the in vivo screen includes the steps of (i) providing BMDCs that lack the candidate gene; (ii) exposing the BMDCs lacking the candidate gene to activating stimulus; (iii) transferring the BMDCs from step (iii) to an animal model; (iv) assessing whether the animal model develops an autoimmune disease, thereby validating the target gene as a candidate target for treatment of autoimmune disease. In a further embodiment, the animal model is a model for a member selected from the group consisting of autoimmune diabetes, multiple sclerosis, and rheumatoid arthritis. In certain embodiments, the activating stimulus can be any known in the art to activate DCs, including without limitation polyinosinic-polycytidylic acid (Poly(I:C)), TLR ligands, *M. tuberculosis* antigens, or *M. tuberculosis* infection.

Example 1: Generation of Mice and Cell Lines

Wild-type C57 BL/6 mice and gene-targeted IL-12/23-p40-eYFP (86.129-Il12b$^{tm1Lky}$/J, Stock Number 006412) knock-in mice were purchased from The Jackson Laboratory. Homozygous RIP-GP ("Berlin$^{+/+}$") mice were previously generated. Heterozygous RIP-GP mice were generated by crossing male Berlie$^{+/+}$) mice with female wild-type C57BL/6 mice. Gene-targeted SHP-deficient (Shp$^{-/-}$) mice on the C57BL/6 genetic background were previously generated. All mice were maintained, and all experiments were performed, at the Ontario Cancer Institute Animal Resource Centre. All procedures were approved by the University Health Network Animal Care Committee.

BMDCs were generated in vitro according to the Lutz method (J Immunol Methods 223, 77-92 (1999)). Briefly, bone marrow cells were harvested from the femurs and tibias of mice and cultured in 100 mm bacteriological Petri dishes (BD Falcon) for ten days in RPMI 1640 (Gibco) containing 10% heat-inactivated FBS (Life Technologies), 55 µM of 2-mercaptoethanol (Gibco), and GM-CSF (40 ng/mL for the first 3 days, 20 ng/mL for the remaining 7 days, PeproTech). Medium was changed on days 3, 6, and 8. On day 10, non-adherent BMDCs were collected for further culture or analysis as described herein. In the case of further culture without electroporation, the non-adherent BMDCs were washed and re-cultured in 24-well plates at $2\times10^6$/mL/well with or without (1) LPS (Sigma) at 1000, 100, 10, or 1 ng/mL or (2) polyinosinic-polycytidylic acid (poly(I:C), Invivogen) at 100 µg/mL for 16-20 hours. Then, BMDCs were collected for further analysis as described herein.

The Nuclear Receptors siGENOME siRNA library (Dharmacon) contained 54 siRNA pools (SMARTpools), each consisting of four synthetic siRNA duplexes targeting a single gene, arrayed in a 96-well plate at 0.5 nmol/well. The Cytokine Receptors siGENOME siRNA library contained 158 SMARTpools. A number of siRNA SMARTpools were purchased and used individually, including Non-Targeting Pool #2, siGLO Red Transfection Indicator, CD11c, A20, SOCS1, NROB2. Lyophilized siRNA library SMARTpools were resuspended in their original library plate in Opti-MEM buffer (Gibco) at 10 mM, then placed on an orbital shaker for 30 minutes at room temperature according to Dharmacon's instructions. Stock solutions of lyophilized individual siRNA SMARTpools were prepared by resuspension in Opti-MEM buffer at 20 µM or 50 µM, followed by orbital shaking.

On day 10 of BMDC culture, non-adherent BMDCs were collected, washed, and resuspended in Opti-MEM buffer at $20\times10^6$/mL. Lyophilized siRNA library SMARTpools arrayed in 96-well plates (0.5 nmol/well) were resuspended and shaken in Opti-MEM at 10 mM as described above, then transferred to a 96-well Bio-Rad Gene Pulser MXCell electroporation plate. To each well of the electroporation plate were added $1.1\times10^6$ BMDCs in 55 µL of Opti-MEM, producing a final cell density of $10.5\times10^6$/mL and a final siRNA concentration of 4762 nM. An exponential waveform pulse of 400 V, 200 µF, and 1000Ω was delivered to each sample well at room temperature. Immediately following electroporation, BMDCs were transferred using adjustable multi-channel pipettes to pre-warmed 24-well plates containing 1 or 2 mL of complete 10% RPMI, then incubated at 37° C. in 5% $CO_2$. Forty-eight hours later, BMDCs were collected by gentle pipetting for further experimentation or analysis. For optimization experiments in which pulse voltage and capacitance were varied, the resistance was always held constant at 1000Ω.

BMDC-T CELL CO-CULTURE: A BMDC-CD3+ T cell co-culture (1:10) with 72 hours of low-dose CD3 monoclonal antibody stimulation (0.1 mg/mL, BioLegend) was prepared in 96-well plates. BMDCs were generated in vitro and electroporated with siRNA as described above. After 48 hours of culture in 24-well plates as described above, supernatants were gently collected and frozen at −80° C. for future cytokine analysis. Two mL of complete RPMI was added back to each well for cell resuspension. In order to promote high-throughput workflow, the number of cells in each well was not determined. Rather, based on previous data, cell recovery per well was assumed to be 60%, considering viability and plastic adherence. Since each well was originally seeded with $1.1\times10^6$ electroporated BMDCs, it was assumed that 48 hours later, there were $0.66\times10^6$ BMDCs in 2 mL in each well. Thus, 30 µL ($0.01\times10^6$ cells) of the BMDC suspension in each well was transferred to separate wells of a 96-well plate. In parallel, CD3+ T cells were purified from wild-type C57BL/6 spleens using a Pan T Isolation Kit II (Miltenyi). Twenty million CD3+ T cells at $10\times10^6$/mL were stained with Violet CellTrace (VCT, Life Technologies) at 2.5 µM for 20 minutes at 37° C. and 5% $CO_2$. Following quenching with complete RPMI, the CD3+ T cells were incubated for another 5 minutes at 37° C. and 5% $CO_2$. After resuspension at $0.476\times10^6$/mL in complete RPMI containing 0.1 mg/mL of CD3 monoclonal antibody, $0.1\times10^6$(210 µL) of the VCT-stained T cells were added to each well of the BMDC-containing 96-well plate above. After 72 hours of co-culture at 37° C. and 5% $CO_2$, all cells were collected, washed, and acquired on a FACSCanto flow cytometer. Cell division and proliferation analyses were performed using FlowJo software.

BMDC VACCINATION OF RAT INSULIN PROMOTER-LYMPHOCYTIC CHORIOMENINGITIS VIRUS GLYCOPROTEIN (RIP-GP) MICE: BMDCs were prepared in vitro as described above. On day 10, non-adherent BMDCs were collected, washed, and re-cultured in 24-well plates at $2\times10^6$/mL/well with or without LPS at 10 ng/mL (Sigma) for 16-20 hours. Then, the BMDCs in each well were pulsed with a triple-peptide mix of LCMV peptides (New England Peptide and Washington Biotechnology) for 2-3 hours as follows: $10^{-6}$ M gp33-41 (KAVYNFA™), $10^{-6}$ M gp276-286 (SGVENPGGYCL), and 1 µg/mL gp61-80 (GLNGPDIYKGVYQFKSVEFD). BMDCs were collected by pipetting up and down, washed with Hanks' Buffered Saline Solution (HBSS), and resuspended in HBSS at $10 \times 10^6$/mL. Two million BMDCs (0.2 mL) were injected intravenously into each RIP-GP mouse via the lateral tail vein. Blood glucose concentrations were measured beginning on day 6 and then every 2-3 days thereafter using an electronic glucometer and chemstrips (Accu-Chek). Diabetes was diagnosed after two consecutive blood glucose readings of 15 mM or higher.

Example 2: Assays

Flow Cytometry Assays

Surface staining: Cells were collected, centrifuged, transferred to flow cytometry tubes, and washed with cold PBS (without calcium and magnesium) containing 2% FBS and 0.09% sodium azide ("Staining Buffer"). After 10 minutes of Fc receptor blockade with CD16/CD32 monoclonal antibodies (BioLegend) at 4° C., cells were stained for 30 minutes at 4° C. in the dark with different combinations of fluorochrome-conjugated monoclonal antibodies, including: MHC II (I-A/I-E or I-A$^b$), CD80, and CD86 (all from BD BioSciences), and CD11c (eBioscience). Cells were washed with cold Staining Buffer, centrifuged, resuspended in Staining Buffer, and acquired on a FACSCanto flow cytometer (BD).

Viability staining: Following surface staining as described above, cells were washed with cold Staining Buffer, centrifuged, and incubated with 50 µL of 7-AAD (BD Biosciences) for 15 minutes at 4° C. in the dark. After adding 200 µL of Staining Buffer to each sample, cells were acquired on a FACSCanto flow cytometer.

Intracellular cytokine staining: Intracellular cytokine staining was performed using the BD Biosciences Cytofix/Cytoperm Fixation/Permeabilization kit according to the manufacturer's instructions. Briefly, cells were incubated with GolgiPlug (Brefeldin A) for 5-6 hours. Following surface staining as described above, cells were washed with cold Staining Buffer and permeabilized by incubation in Cytofix/Cytoperm for 30 minutes at 4° C. Cells were then washed in Perm/Wash buffer and stained with IL-12-p70-specific monoclonal antibody (BD Biosciences) for 30 minutes at 4° C. in the dark. Following additional washes in PermWash buffer, cells were acquired on a FACSCanto flow cytometer.

Data analysis: Flow cytometry data was analyzed using FlowJo software (Tree Star). When more than one fluorochrome was used, single-stained compensation controls were acquired for compensation analysis, which was always manually performed in FlowJo. Cellular debris was excluded from analysis by setting an appropriate gate in the forward scatter (FSC)/side scatter (SSC) plot. All other gates were set based on fluorescence-minus-one (FMO) control samples. Except for IL-12/23-p40-YFP knock-in BMDCs, all other BMDCs were gated on the CD11c$^{high}$ population before analysis. The CD11c$^{high}$ population frequency was approximately 90% of the FSC/SSC population. IL-12/23-p40-YFP BMDCs were gated on the FSC/SSC population, then analyzed for YFP expression. When viability staining was performed, analyses were conducted on live cells by gating on the 7-AAD-negative population. All MFI values represent median fluorescent intensities. For some histogram overlays, the data were normalized to the peak height at the mode of the distribution (i.e., the number of cells in each bin of a given histogram was divided by the number of cells in the bin containing the largest number of cells). Thus, the y-axis depicts the percentage of the maximum number of cells (i.e., the number of cells at the mode of the distribution).

FITC-DEXTRAN ENDOCYTOSIS ASSAY: BMDCs were collected, centrifuged, washed, and resuspended in 180 µL of complete RPMI. Twenty microlitres of fluorescein isothiocyanate-dextran (FITC-DX, 10 mg/mL, Sigma) was added to produce a final FITC-DX concentration of 1 mg/mL. Control samples (surface binding of FITC-DX but no endocytosis) were incubated for 30 minutes at 4° C. in the dark while experimental samples (surface binding and endocytosis) were incubated for 30 minutes at 37° C. and 5% $CO_2$ in the dark. After three washes in ice cold Staining Buffer, cells were incubated with Fc block as described above, then surface-stained with MHC II (I-A/I-E)-specific monoclonal antibody (BD Biosciences) for 30 minutes at 4° C. in the dark. Cells were washed and then acquired on a FACSCanto flow cytometer.

CYTOKINE ELISA: BMDC culture supernatants were collected 48 hours after siRNA library transfection and stored at −80° C. for future cytokine ELISA analysis. The concentrations of IL-6, IL-12-p70, and TNF-α were determined by sandwich ELISA analysis according to the manufacturer's guidelines (eBioscience Ready-SET-Go! kits).

Example 3: Testing the Effect of FBS on BMDC Maturation Level

Figure 3:
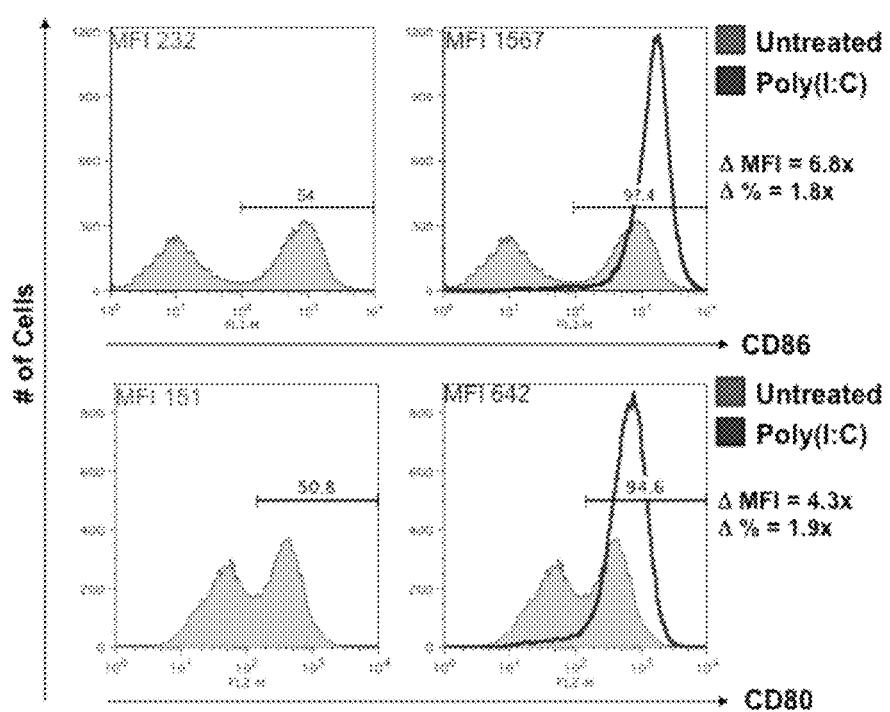
FIG. 3 shows data on CD80 and CD86 expression in BMDCs before optimization.

To maximize the dynamic range of the screen (i.e., to maximize the probability of detecting a true phenotypic change resulting from BMDC gene silencing), BMDCs with minimal baseline maturation were generated (i.e., as phenotypically immature as possible, while retaining the ability to become fully activated) prior to transfection. Before optimization, the baseline expression of CD80 and CD86 on the surface of the BMDCs was relatively high (FIG. 3). For the data in FIG. 3, resting BMDCs were generated by culturing WT C57BL/6 bone marrow cells in the presence of GM-CSF for 10 days. On day 10, BMDCs were left unstimulated or stimulated with poly(I:C). After 16-20 hours of culture, BMDCs were stained with fluorochrome-conjugated monoclonal antibodies and analyzed by flow cytometry. Cells were gated on the CD11chigh population. Top row histograms: Surface CD86 expression. Bottom row histograms: Surface CD80 expression. Filled (solid) histograms: Unstimulated BMDCs. Open (line) histograms: Poly (I:C)-stimulated BMDCs. Numbers indicate (1) the frequency of CD80+ and CD86+ populations, (2) the MFI of CD80 and CD86 expression, and (3) the fold-change in CD80+/CD86+ population frequency and CD80/CD86 MFI upon poly(I:C) stimulation. Data are representative of many independent experiments.

The biochemical profile of the fetal bovine serum (FBS) used to generate BMDCs in vitro can have an effect on their differentiation and baseline maturation level. A review of the certificate of analysis of the FBS lot for the BMDC cultures used for the data generated in FIG. 3 showed the LDH and SGOT concentrations in the FBS were 2136 mU/mL and 148 mU/mL, respectively. These values were greatly in excess of the threshold level for BMDC-stimulating FBS determined by Lutz et al.

Figure 4:
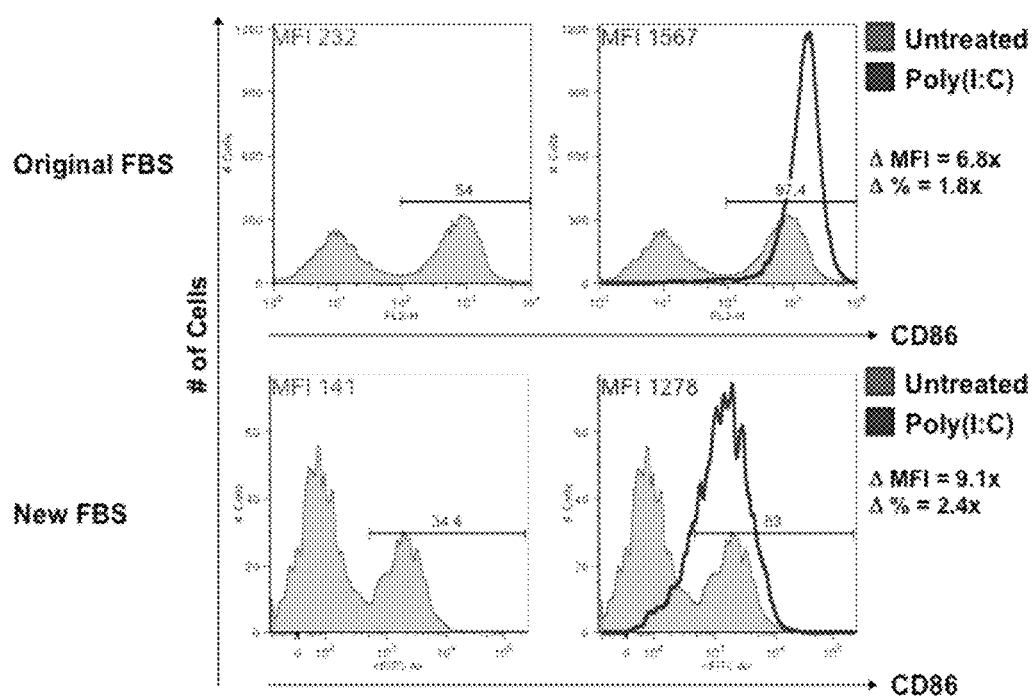
FIG. 4 shows the effect of LDH and SGOT concentrations on BMDC maturation level.

Several new FBS lots, all with LDH and SGOT concentrations between 300-700 mU/mL and 12-50 mU/mL, respectively were tested for their effects on BMDC differentiation and maturation. FIG. 4 shows a representative experiment in which BMDCs were generated using one of the new FBS lots (Invitrogen, Catalog No. 16000, Lot No. 432023, [LDH]=332 mU/mL, [SGOT]=31 mU/mL). Resting BMDCs were generated by culturing WT C57BL/6 bone marrow cells in the presence of GM-CSF for 10 days, either with original (pre-optimization) FBS or new FBS containing [LDH] and [SGOT] within the ranges recommended by Lutz et al. On day 10, BMDCs were left unstimulated or stimulated with poly(I:C). After 16-20 hours of culture, BMDCs were stained with fluorochrome-conjugated monoclonal antibodies and analyzed by flow cytometry. Cells were gated on the $CD11c^{high}$ population. FIG. 4: Top row histograms: Surface CD86 expression on BMDCs cultured in original FBS. Bottom row histograms: Surface CD86 expression on BMDCs cultured in new FBS. Filled in (solid) histograms: Unstimulated BMDCs. Open (line) histograms: Poly(I:C)-stimulated BMDCs. Numbers indicate (1) the frequency of the CD86+ population, (2) the MFI of CD86 expression, and (3) the fold-change in CD86+ population frequency and CD86 MFI upon poly(I:C) stimulation. Data are representative of at least three independent experiments.

Figure 5:
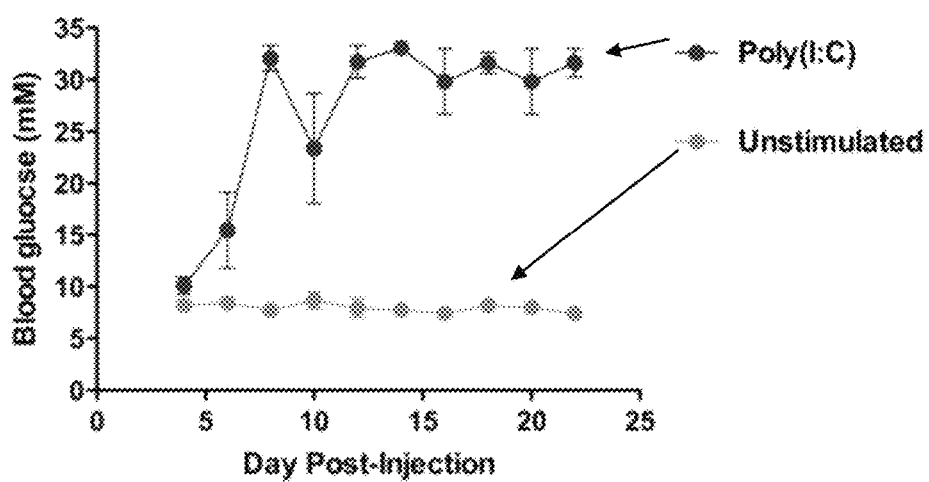
FIG. 5 shows data from RIP-GP mice injected with stimulated and unstimulated BMDCs.

As compared to the relatively high frequency of CD86+ BMDCs (54%) that was generated using the old FBS, the CD86+ frequency that was generated with the new FBS was reduced by more than one-third (to 34%). Importantly, the BMDCs generated using the new FBS lot retained the ability to become activated in response to TLR-ligand stimulation, as evidenced by the expected rise in the CD86+ frequency (old FBS: 1.8-fold, new FBS: 2.4-fold) and CD86MFI (old FBS: 6.8-fold, new FBS: 9.1-fold). In addition, unstimulated BMDCs generated using the new FBS lot did not induce autoimmune diabetes when they were LCMV peptide-pulsed and transferred into RIP-GP mice, whereas poly(I:C)-stimulated, LCMV peptide-pulsed, RIP-GP-transferred BMDCs did induce diabetes (FIG. 5). Resting BMDCs were generated by culturing WT C57BL/6 bone marrow cells in the presence of GM-CSF for 10 days with the new Invitrogen FBS (Catalog No. 16000, Lot No. 432023). On day 10, BMDCs were left unstimulated or stimulated with poly(I:C). After 16-20 hours of culture, BMDCs were pulsed with LCMV triple-peptide mix for 2-3 hours, then adoptively transferred into RIP-GP mice. Data are representative of many independent experiments.

Example 4: Electroporation Achieves High siRNA Transfection Efficiency with Minimal Effect on BMDC Maturation and Viability Electroporation conditions that would simultaneously achieve (1) maximum siRNA transfection efficiency, (2) minimum BMDC maturation, and (3) maximum BMDC viability were investigated. Different sets of electroporation conditions were tested, including different pulse voltages and capacitances, siRNA concentrations, and BMDC densities. The overall strategy was to first exclude electroporation pulse voltage and capacitance parameter sets that resulted in (1) excessive BMDC death, as measured by 7-AAD positivity, and (2) excessive BMDC maturation, as measured by surface BMDC expression of CD80 and CD86. Then, focusing on the subset of electrical parameters that resulted in reasonable BMDC viability and baseline maturation level, the sample siRNA concentration and BMDC density were adjusted in order to achieve maximum transfection efficiency, as measured by BMDC expression of a fluorescently labeled oligonucleotide siRNA duplex (Dharmacon siGLO Red Transfection Indicator).

Figure 6:
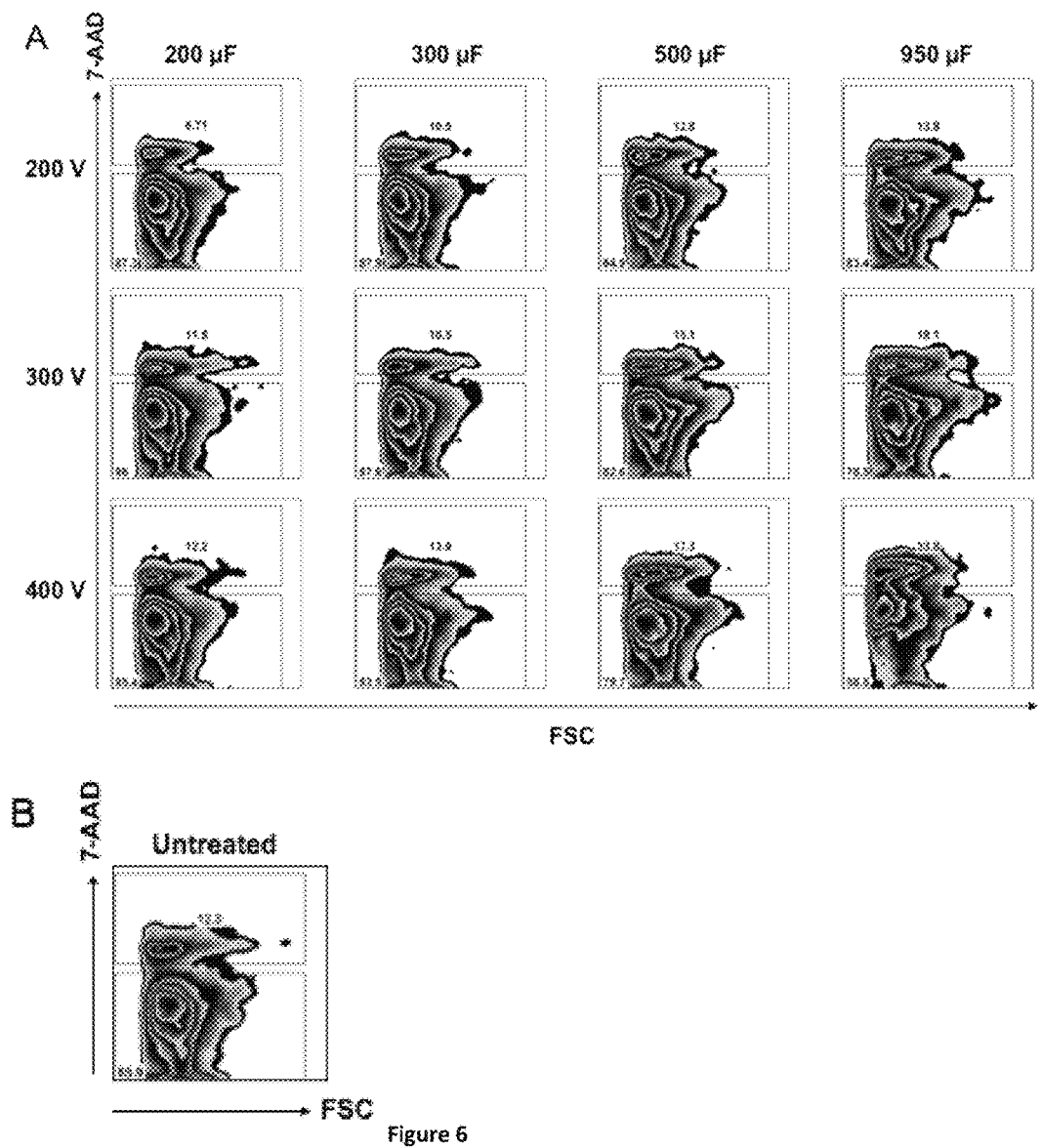
FIG. 6 shows BMDC viability as a function of electroporation pulse voltage and capacitance gradients.

To assess BMDC viability as a function of different electroporation conditions, unstimulated BMDCs were electroporated on day 10 without siRNA (i.e., mock electroporation), then cultured for an additional 48 hours in order to simulate a period of siRNA-mediated gene silencing. At any given voltage, increasing the capacitance resulted in increased BMDC death, as measured by flow cytometric analysis of 7-AAD+ cells (FIG. 6). BMDC death was further increased when voltage and capacitance were concurrently increased. At the same time, these data indicated that over a considerable range of voltages and capacitances, BMDC viability was relatively unaffected (FIG. 6).

Figure 7:
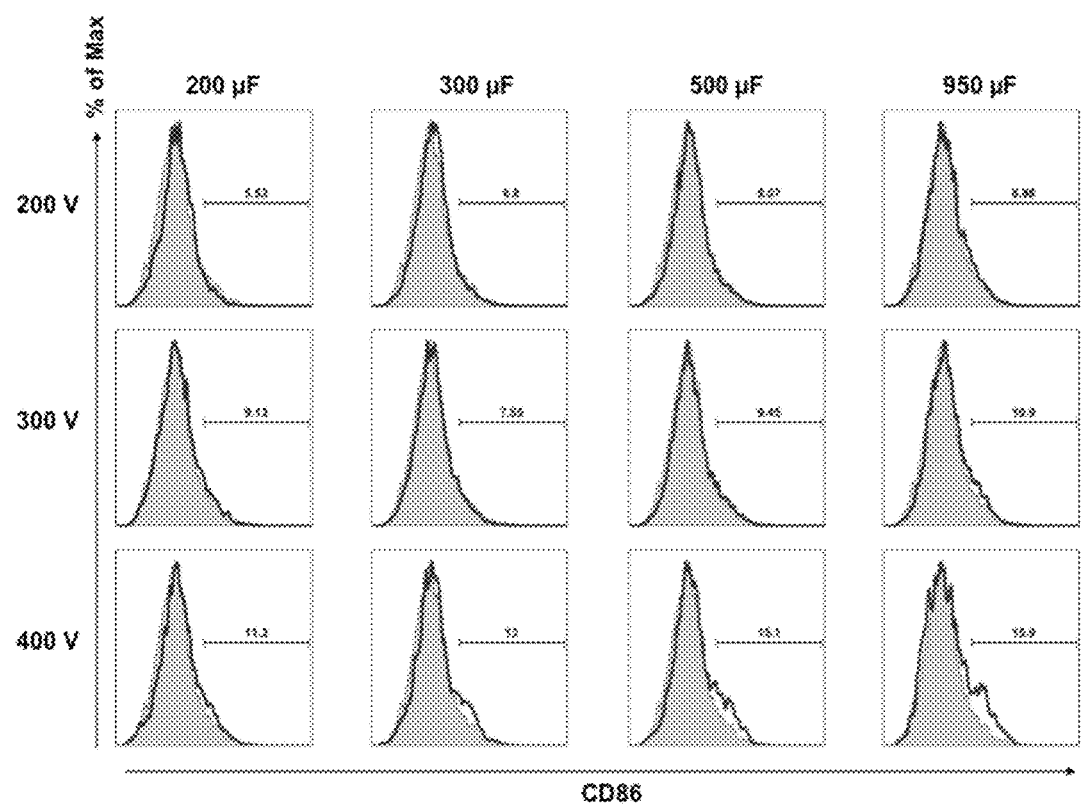
FIG. 7 shows CD86 expression on BMDCs as a function of electroporation pulse voltage and capacitance gradients.

To assess BMDC maturation level as a function of different electroporation conditions, unstimulated BMDCs were electroporated on day 10 without siRNA and cultured for 48 hours in order to simulate a period of siRNA-mediated gene silencing. Only at a pulse voltage level of 400 V was there any increase in CD86 expression, which was further augmented as the pulse capacitance was increased (FIG. 7).

On the basis of these BMDC viability and maturation data, the delivery of a pulse capacitance of 950 µF appeared to be excessive and undesirable, regardless of the pulse voltage level. This conclusion was supported by the data of Jantsch et al. (J Immunol Methods 337, 71-77 (2008).), who used a pulse of 400 V/150 µF to achieve excellent gene silencing at the RNA and protein levels.

To optimize siRNA transfection efficiency, the uptake of a fluorescently labeled oligonucleotide duplex (siGLO Red Transfection Indicator, Dharmacon) was studied as a function of siRNA concentration, BMDC density, and a refined, narrower gradient of pulse voltages and capacitances. siGLO Red uptake was analyzed by flow cytometry, performed immediately following electroporation.

Figure 8A:
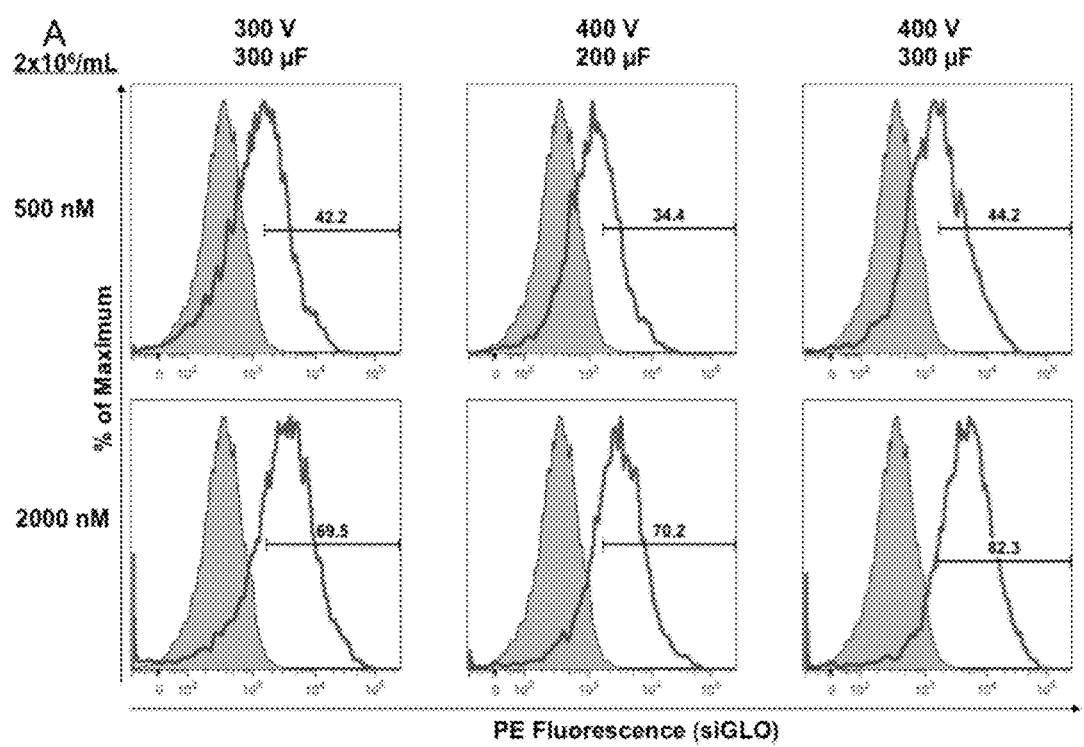
FIGS. 8A and B show siRNA transfection efficiency as a function of [siRNA], BMDC density, and pulse voltage and capacitance gradients.
Figure 8B:
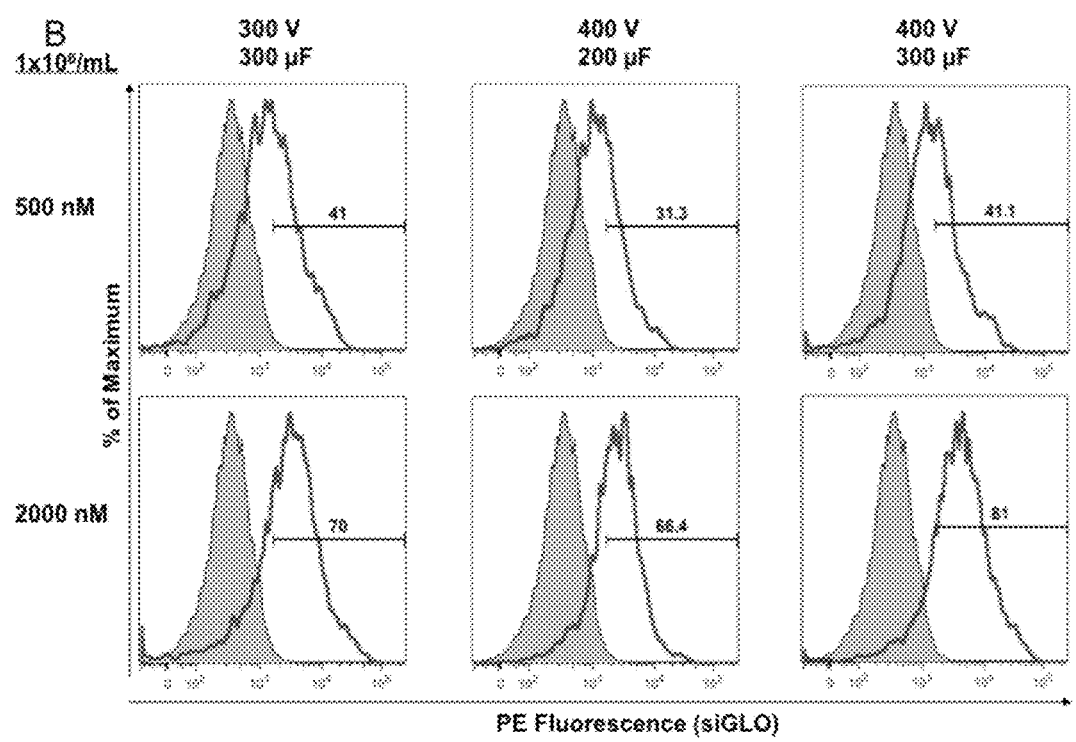

FIG. 8 shows representative results from this initial set of experiments. Even at the relatively high siRNA concentration of 500 nM, the transfection efficiency was only between 30-45%. However, when the siRNA concentration was increased greatly to 2000 nM, the transfection efficiency rose to 65-80%. When the BMDC density was doubled from $1\times10^6$/mL to $2\times10^6$/mL (while holding pulse voltages and capacitances constant), there was no significant change in the transfection efficiency at either 500 nM or 2000 nM. However, when the pulse capacitance and siRNA concentration were held constant at 300 µF and 2000 nM, respectively, increasing the pulse voltage from 300 V to 400 V raised the transfection efficiency by more than 10% (from 70% to 80% at either BMDC density). Similarly, when the pulse voltage and siRNA concentrations were held constant at 400 V and 2000 nM, respectively, increasing the pulse capacitance from 200 µF to 300 µF raised the transfection efficiency by more than 10% at both BMDC densities (70 to 80%). At the siGLO concentration of 2000 nM and the BMDC density of either $1\times10^6$/mL or $2\times10^6$/mL, there was no significant difference in transfection efficiency when the pulse voltage and capacitance were varied in opposite directions, i.e., to either 300 V/300 µF or 400 V/200 µF. For the experiments in FIG. 8, resting BMDCs were generated by culturing WT C57BL/6 bone marrow cells in the presence of GM-CSF for 10 days. On day 10, BMDCs were electroporated with either a fluorescently labeled siRNA (siGLO) or a non-fluorescent, non-targeting (NT) control. Cells were analyzed by flow cytometry following electroporation. Cells were gated on the FSC/SSC population. Filled in (solid) histograms: NT control. Open (line) histograms: siGLO. Rows show different siGLO concentrations. Columns show different pulse voltages and capacitances. Numbers indicate the transfection frequency, i.e., the frequency of siGLO+ BMDCs. (A) BMDC density=$2\times10^6$/mL. Data are representative of at least two independent experiments.

On the basis of these results, it appeared that (1) maximum transfection efficiency may require the siRNA concentration to be at least 2000 nM, (2) there was no advantage or disadvantage to doubling the BMDC density from $1\times10^6$/mL to $2\times10^6$/mL when the siGLO concentration was high at 2000 nM, and (3) applying a pulse of 400 V/300 µF achieved the highest transfection efficiency, but at the cost of (a) slightly more BMDC death (FIG. 6) and (b) slightly more CD86 expression (FIG. 7). By comparison, delivering a pulse of 400 V/200 µF resulted in marginally less transfection efficiency, but also slightly less BMDC death and maturation.

For the data in FIG. 6, resting BMDCs were generated by culturing WT C57BL/6 bone marrow cells in the presence of GM-CSF for 10 days. On day 10, BMDCs were left untreated or electroporated without siRNA (mock electroporation) with different pulse voltages and capacitances. After 48 hours of culture, BMDCs were stained with 7-AAD and analyzed by flow cytometry. Cells were gated on the FSC/SSC population. (A) Plots of the 7-AAD+ and 7-AAD− populations as a function of pulse voltage and capacitance. (B) Plot of the 7-AAD+ and 7-AAD− populations in the untreated (non-electroporated) control. Numbers indicate the frequency of 7-AAD+ and 7-AAD-populations. Data are representative of two independent experiments.

For the data in FIG. 7: resting BMDCs were generated by culturing WT C57BL/60 bone marrow cells in the presence of GM-CSF for 10 days. On day 10, BMDCs were left untreated or electroporated without siRNA (mock electroporation) with different pulse voltages and capacitances. After 48 hours of culture, BMDCs were stained with fluorochrome-conjugated monoclonal antibodies and analyzed by flow cytometry. Cells were gated on the 7-AAD−, CD11chigh population. Filled in (solid) histograms: CD86 expression as a function of pulse voltage and capacitance. Line (open) histograms: CD86 expression in the untreated (non-electroporated) control. Numbers indicate the CD86+ frequency. Data are representative of at least two independent experiments.

These results led to new optimization experiments focusing on an even narrower range of electroporation conditions. Specifically, comparisons were made between (1) a pulse of 400 V/200 µF to a pulse of 400 V/150 µF, (2) an escalating gradient of siRNA concentrations from 2000 nM to 4762 nM, and (3) and escalating gradient of BMDC densities from $2\times10^6$/mL to $20\times10^6$/mL.

Figure 9:
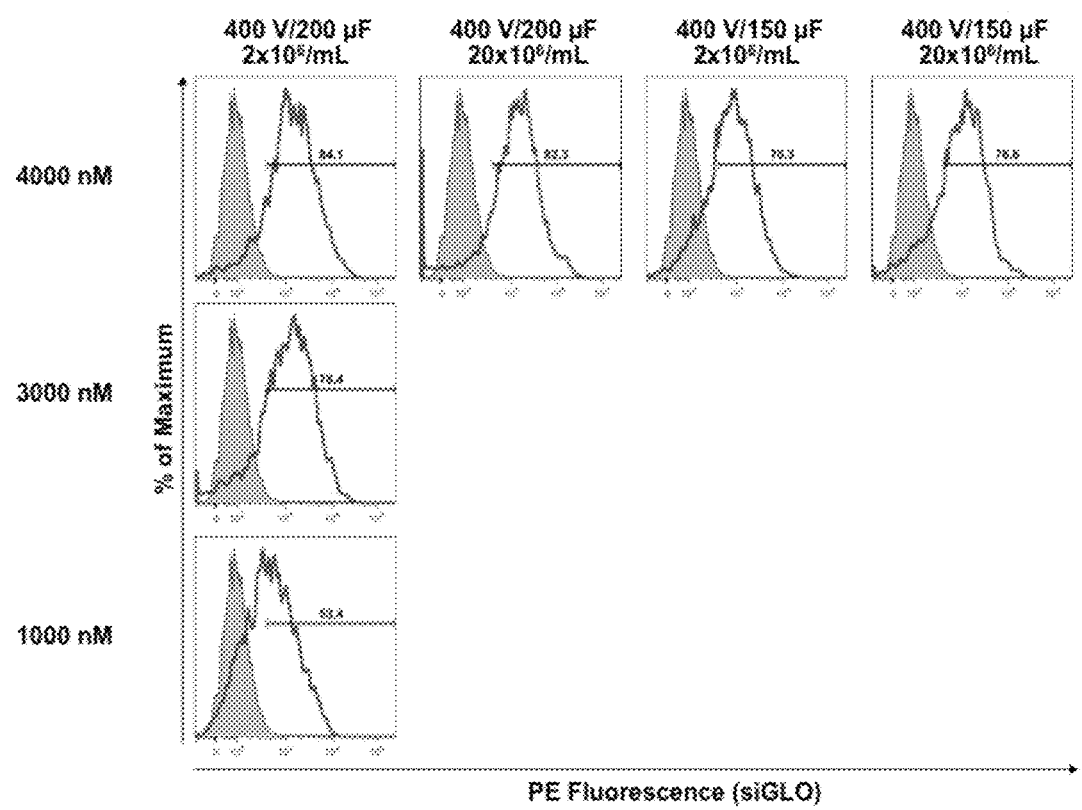
FIG. 9 shows siRNA transfection efficiency as a function of [siRNA], BMDC density, and focused pulse voltage and capacitance gradients.

FIG. 9 shows representative results from the first set of these experiments. At the BMDC density of $2\times10^6$/mL, electroporating 4000 nM of siRNA resulted in a higher transfection efficiency (85%) than either 3000 nM (80%) or 1000 nM (50%) of siRNA. At the siRNA concentration of 4000 nM, there was no advantage or disadvantage in raising the BMDC density to $20\times10^6$/mL from $2\times10^6$/mL (both 80-85%). Notably, when the pulse voltage was maintained at 400 V but the pulse capacitance was reduced from 200 µF to 150 µF to simulate Jantsch et al.'s conditions, the transfection efficiency dropped substantially from 85% to 70% (BMDC density held constant at $2\times10^6$/mL). This drop was slightly attenuated when the BMDC density was raised to Jantsch et al.'s level of $20\times10^6$/mL.

From these results, it appears that (1) maximum transfection efficiency would require at least 4000 nM of siRNA, (2) a pulse of 400 V/200 µF was superior to a pulse of 400 V/150 µF, and (3) high transfection efficiency could be achieved over a 10-fold range of BMDC densities (2-$20\times10^6$/mL).

For the data in FIG. 9, resting BMDCs were generated by culturing WT C57BL/6 bone marrow cells in the presence of GM-CSF for 10 days. On day 10, BMDCs were electroporated with either a fluorescently labeled siRNA (siGLO) or a non-fluorescent, non-targeting (NT) control. Cells were analyzed by flow cytometry following electroporation. Cells were gated on the FSC/SSC population. Filled in (solid) histograms: NT control. Open (line) histograms: siGLO. Rows show different siGLO concentrations. Columns show different pulse voltages, pulse capacitances, and BMDC densities. Numbers indicate the transfection frequency, i.e., the frequency of siGLO+ BMDCs. Data are representative of at least two independent experiments.

To facilitate high-throughput screening, it was desirable to electroporate a sufficient number of cells to permit multiple functional assays from a single electroporation experiment. Thus, an experiment was designed to determine whether high transfection efficiency could be achieved at the BMDC density of $10.5\times10^6$/mL (FIG. 10). At an electroporation sample volume of 105 µL, this BMDC density corresponded to an absolute BMDC number of $1.1\times10^6$/well. This number was advantageous, as it permitted division of the electroporated BMDCs from each well of the electroporation plate into two separate 24-plate wells, each containing approximately $5.5\times10^5$ BMDCs. After 48 hours of putative gene silencing, and allowing for an expected degree of BMDC death, these divided samples containing $5.5\times10^5$ BMDCs each were suitable for at least three functional assays (e.g., flow cytometric analysis of cell surface markers, flow cytometric analysis of FITC-DX uptake, and ELISA analysis of cytokine production).

Resting BMDCs were generated by culturing WT C57BL/6 bone marrow cells in the presence of GM-CSF for 10 days. On day 10, BMDCs were electroporated with either a fluorescently labeled siRNA (siGLO) or a non-fluorescent, non-targeting (NT) control. Cells were analyzed by flow cytometry following electroporation. Cells were gated on the FSC/SSC population. Filled in (solid) histograms: NT control. Line (open) histograms: siGLO. (A) Histograms showing transfection efficiency (i.e., the frequency of siGLO+ BMDCs). (B) Summary data from multiple independent experiments.

Figure 10A:
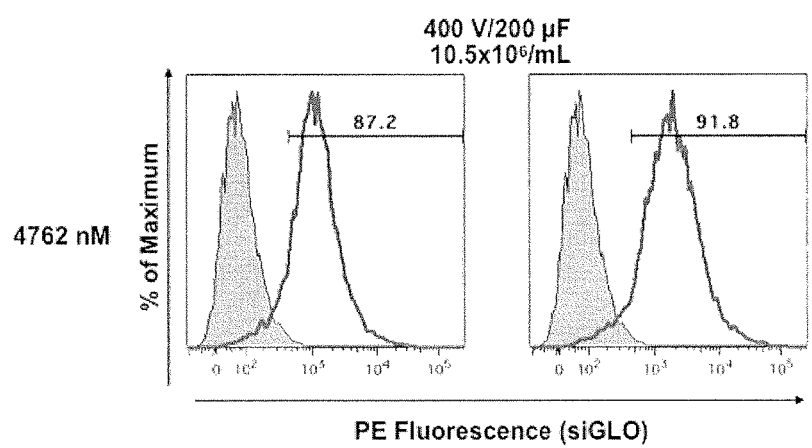
FIGS. 10A and 10B show transfection efficiency data showing that optimized siRNA transfection efficiency approaches 90% under conditions described herein.
Figure 10B:
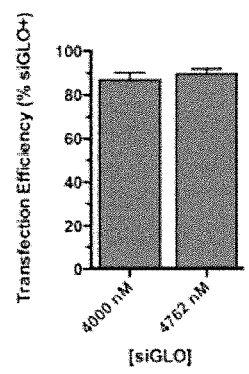

To test transfection efficiency at the BMDC density of $10.5\times10^6$/mL, the siRNA concentration was increased to 4762 nM in order to (1) promote technical simplicity, because each well of the Dharmacon siRNA libraries contained 0.5 nmol of pre-spotted, lyophilized siRNA (0.5 nmol/105 µL=4762 nM), and (2) more closely simulate the electroporation conditions of Jantsch et al., who used approximately 4800 nM of siRNA. FIG. 10A shows that at the BMDC density of $10.5\times10^6$/mL and the siRNA concentration of 4762 nM, the transfection efficiency was extremely high, approaching 90%. FIG. 10B shows representative summary data from multiple transfection efficiency experiments performed using 4000 nM or 4762 nM of siRNA. On the basis of these results, it appears that the ideal electroporation conditions for the siRNA library screen included the combination of: (1) a pulse of 400 V/200 µF, (2) an siRNA concentration of 4762 nM, and (3) a BMDC density of $10.5\times10^6$/mL.

Figure 11:
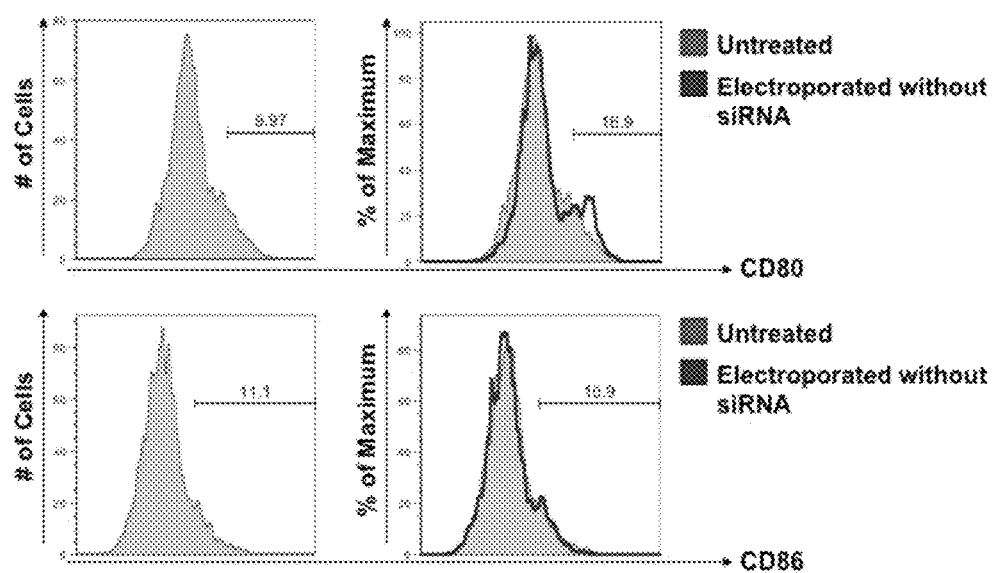
FIG. 11 shows BMDC viability and maturation under identified electroporation conditions.

The optimized transfection efficiency allowed an investigation of BMDC viability and maturation, in order to confirm that the optimized electroporation conditions would not cause excessive BMDC death or maturation. FIG. 11 shows that electroporating $10.5\times10^6$/mL BMDCs with a pulse of 400 V/200 µF (without siRNA) resulted in no change in surface CD86 expression and only a minimal increase in CD80 expression. Resting BMDCs were generated by culturing WT C57BL/6 bone marrow cells in the presence of GM-CSF for 10 days. On day 10, BMDCs were left untreated or electroporated without siRNA (mock electroporation) with a pulse of 400 V/200 µF at a cell density of $10.5 \times 10^6$/mL. After 48 hours of culture, BMDCs were stained with fluorochrome-conjugated monoclonal antibodies and analyzed by flow cytometry. Cells were gated on the 7-AAD−, CD11c$^{high}$ population. Top row histograms: CD80 expression. Bottom row histograms: CD86 expression. Filled in (solid) histograms: Untreated samples. Line (open) histograms: Mock-electroporated samples. Numbers indicate CD80+ and CD86+ frequencies. Data are representative of multiple independent experiments.

Figure 12:
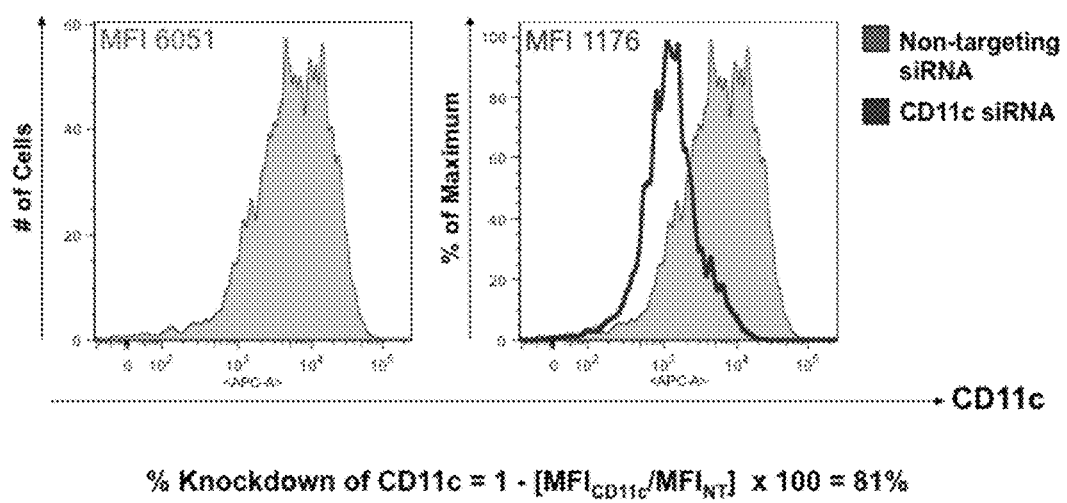
FIG. 12 shows data from transfection of CD11c-specific siRNA as measured by flow cytometry.

Example 5: Transfection of siRNA Targeting a Known Negative Regulator of BMDC Activation Induces BMDC Maturation Control experiments were conducted to confirm that gene expression in BMDCs could be successfully downregulated using siRNA. These experiments were directed to silencing the CD11c gene, whose protein product is highly expressed and easily detectable on the BMDC surface. FIG. 12 shows that transfection of CD11c-specific siRNA caused a greater than 80% reduction of surface CD11c expression, as measured by flow cytometry. Resting BMDCs were generated by culturing WT C57BL/6 bone marrow cells in the presence of GM-CSF for 10 days. On day 10, BMDCs were electroporated with CD11c-specific siRNA or NT siRNA (4762 nM) with a pulse of 400 V/200 µF at a cell density of $10.5 \times 106$/mL. After 48 hours of culture, BMDCs were stained with fluorochrome-conjugated monoclonal antibodies and analyzed by flow cytometry. Cells were gated on the 7-AAD- population. Histograms show CD11c expression. Filled in (solid) histogram: NT siRNA-transfected samples. Line (open) histogram: CD11c siRNA-transfected sample. Data are representative of at least three independent experiments.

Induction of BMDC maturation by transfecting siRNA targeting SOCS1, a known negative regulator of DC activation was also tested. Transfection of SOCS1-specific siRNA caused a substantial increase in BMDC maturation, as indicated by (1) an increase in BMDC surface expression of CD86 and CD80 (FIG. 13), (2) an increase in the MHC II$^{high}$/DX$^{neg}$ population frequency, and (3) a decrease in the MHC II$^{low}$/DX$^{pos}$ population frequency (FIG. 14).

Figure 13:
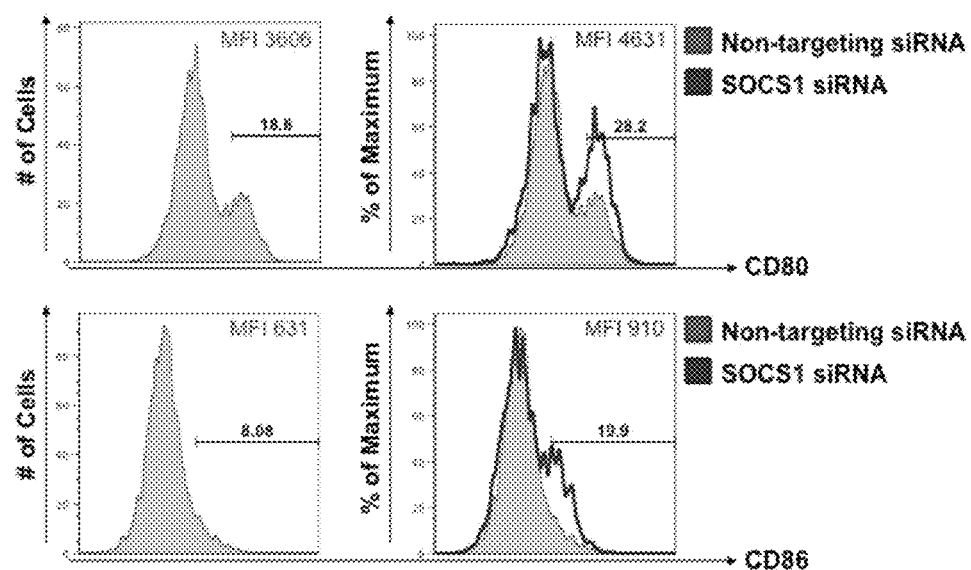
FIG. 13 shows the effect of transfection of SOCS1-specific siRNA on BMDC maturation.

For the data in FIG. 13, resting BMDCs were generated by culturing WT C57BL/6 bone marrow cells in the presence of GM-CSF for 10 days. On day 10, BMDCs were electroporated with SOCS1-specific siRNA or NT siRNA (4762 nM) with a pulse of 400 V/200 µF at a cell density of 10.5=106/mL. After 48 hours of culture, BMDCs were stained with fluorochrome-conjugated monoclonal antibodies and analyzed by flow cytometry. Cells were gated on the 7-AAD−, CD11chigh population. Top row histograms: CD80 expression. Bottom row histograms: CD86 expression. Filled in (solid) histograms: NT siRNA-transfected samples. Line (open) histograms: SOCS1 siRNA-transfected samples. Numbers indicate CD80+ and CD86+ frequencies and CD80 and CD86 MFIs. Data are representative of at least three independent experiments.

Figure 14:
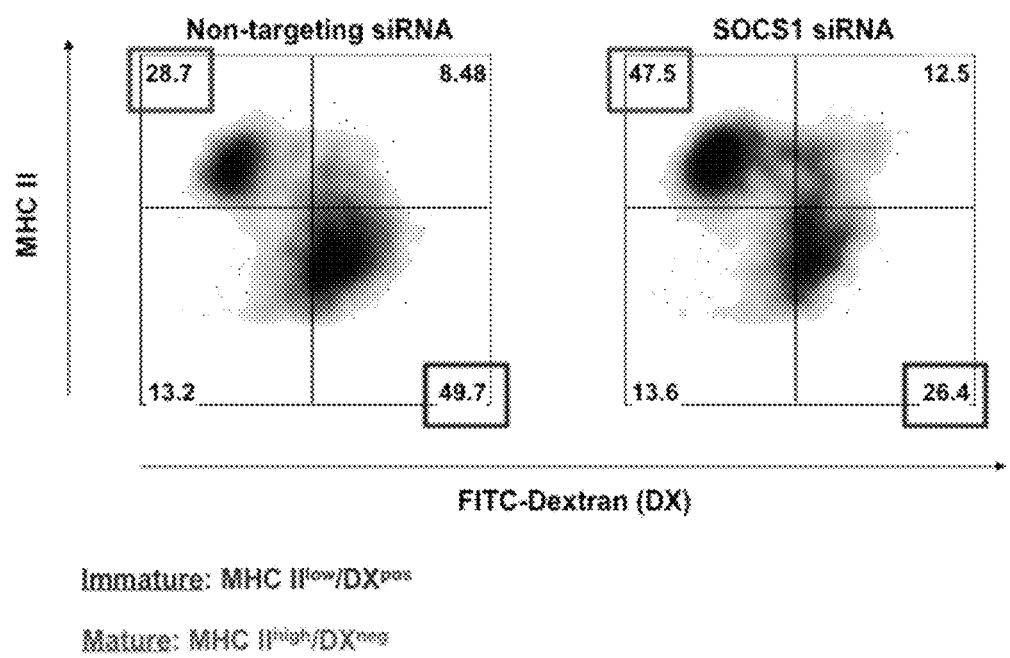
FIG. 14 shows the effect of transfection of SOCS1-specific siRNA on BMDC maturation.

For the data in FIG. 14, Resting BMDCs were generated by culturing WT C57BL/6 bone marrow cells in the presence of GM-CSF for 10 days. On day 10, BMDCs were electroporated with SOCS1-specific siRNA or NT siRNA (4762 nM) with a pulse of 400 V/200 µF at a cell density of $10.5 \times 10^6$/mL. After 48 hours of culture, BMDCs were incubated with FITC-DX, then stained with fluorochrome-conjugated monoclonal antibodies and analyzed by flow cytometry. Cells were gated on the 7-AAD− population. Density plots show MHC II expression and DX positivity. Data are representative of at least three independent experiments. Immature (top left quadrant rectangles) and Mature (bottom right quadrant rectangles) frequencies are identified.

Example 6: siRNA Library Screen Based On Bmdc Expression Of Il-12/23-P40

In a revised screening approach, it was investigated whether the transfection of siRNAs targeting various cytokine receptor genes (Dharmacon siGENOME siRNA Cytokine Receptors library, 158 SMARTpools) would cause the upregulation of IL-12/23-p 40 production by BMDCs. Upregulation of BMDC-derived IL-12/23-p40 would indicate that the putatively silenced genes were negative regulators of BMDC activation.

Figure 15:
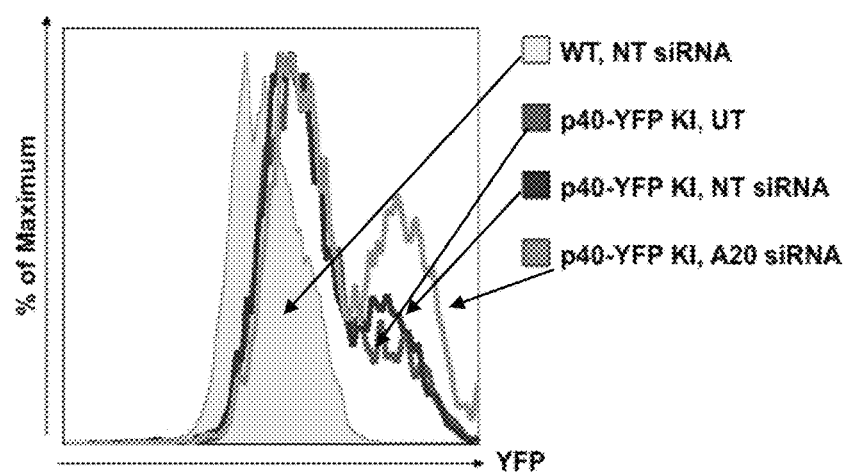
FIG. 15 shows data on fluorescence intensity of BMDCs under several conditions.

A first step was to characterize the estimated dynamic range of this screening approach. To that end, the fluorescence intensity of BMDCs under several key conditions was measured (FIG. 15). As compared to NT siRNA-transfected WT (i.e., eYFP$^{neg}$) BMDCs, a mild increase in eYFP expression in unstimulated (1) non-electroporated p40-eYEP KI BMDCs and (2) NT siRNA-transfected p40-eYFP KI BMDCs was detected. Importantly, there was no significant difference in eYFP expression between these two groups. Moreover, when p40-eYFP KI BMDCs were transfected with siRNA targeting A20 (TNFAIP3, a known negative regulator of DC activation), an upregulation of eYFP expression significantly above the basal level expressed by control NT siRNA-transfected p40-eYFP KI BMDCs was detected.

On the basis of (1) the reasonably low level of eYFP expression in NT siRNA-transfected p40-eYFP KI BMDCs (the control baseline), and (2) the significant eYFP upregulation in A20 siRNA-transfected p40-eYFP KI BMDCs, it appeared that BMDC-derived IL-12/23-p40 production, as detected by eYFP expression in p40-eYFP KI BMDCs, could be used as a robust indicator of BMDC maturation in an in vitro siRNA screen to identify genes that regulate BMDC activation.

For the data in FIG. 15, resting BMDCs were generated by culturing WT C57BL/6 or IL-12/23-p40-YFP knock-in (p40-YFP KI) bone marrow cells in the presence of GM-CSF for 10 days. On day 10, BMDCs were left untreated or electroporated with A20-specific siRNA or NT siRNA (4762 nM) with a pulse of 400 V/200 µF at a cell density of $10.5 \times 10^6$/mL. After 48 hours of culture, BMDCs were analyzed by flow cytometry. Cells were gated on the FSC/SSC population. Data are representative of at least three independent experiments.

The present specification provides a complete description of the methodologies, systems and/or structures and uses thereof in example aspects of the presently-described technology. Although various aspects of this technology have been described above with a certain degree of particularity, or with reference to one or more individual aspects, those skilled in the art could make numerous alterations to the disclosed aspects without departing from the spirit or scope of the technology hereof. Since many aspects can be made without departing from the spirit and scope of the presently described technology, the appropriate scope resides in the claims hereinafter appended. Other aspects are therefore contemplated. Furthermore, it should be understood that any operations may be performed in any order, unless explicitly claimed otherwise or a specific order is inherently necessitated by the claim language. It is intended that all matter contained in the above description and shown in the accompanying drawings shall be interpreted as illustrative only of particular aspects and are not limiting to the embodiments shown. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes. Changes in detail or structure may be made without departing from the basic elements of the present technology as defined in the following claims.

What is claimed:

1. A method for identifying one or more target genes that modulate activation state of dendritic cells, the method comprising:
    (a) transfecting immature bone marrow-derived dendritic cells (BMDCs) with an siRNA library by electroporation;
    (b) detecting whether the BMDCs are in an activated or an inactivated state, thereby identifying one or more target genes that modulate activation state of dendritic cells; and
    (c) validating the one or more target genes that modulate activation state of dendritic cells in an in vivo screen to determine whether the one or more target genes are a candidate target for treatment of autoimmune disease, wherein the in vivo screen comprises:
        (i) providing BMDCs that lack the one or more target genes identified in step (b) wherein the BMDCs are generated from a mouse strain in which the target gene or genes identified in step (b) are genetically ablated;
        (ii) exposing the BMDCs lacking the one or more target genes to activating stimulus;
        (iii) transferring the BMDCs from step (ii) to an animal model;
        (iv) assessing whether the animal model develops an autoimmune disease, thereby validating whether the target gene is a candidate target for treatment of autoimmune disease.

2. The method of claim 1, wherein the detecting step (b) comprises detection of a dendritic cell intrinsic effector function.

3. The method of claim 2, wherein the dendritic cell intrinsic effector function comprises expression of one or more of a member selected from the group consisting of: IL-12/23-p40, CD80, CD86, and MHCII.

4. The method of claim 1, wherein the detecting activation step (b) is conducted using flow cytometry.

5. The method of claim 1, wherein the animal model is a model for a member selected from the group consisting of autoimmune diabetes, multiple sclerosis, and rheumatoid arthritis.

6. The method of claim 1, wherein the siRNA library comprises siRNAs directed to transmembrane receptors.

7. The method of claim 1, wherein the BMDCs from (a) are transfected with an siRNA library by electroporation under conditions comprising at least 2000 nM of siRNA and a pulse of 400V/200 µF.

* * * * *